United States Patent [19]

Chareire et al.

[11] Patent Number: 4,904,255

[45] Date of Patent: * Feb. 27, 1990

[54] COMPLETE ARTIFICIAL HEART WITH TWO PUMPING MODULES CONNECTED TOGETHER BY A FUNCTIONAL CONNECTION

[75] Inventors: Jean-Louis Chareire, Levallois; Didier Lapeyre, Pacy-Sur-Eure, both of France

[73] Assignee: Aerospatiale Societe Nationale Industrielle, Paris, France

[*] Notice: The portion of the term of this patent subsequent to Nov. 18, 2003 has been disclaimed.

[21] Appl. No.: 942,272

[22] Filed: Dec. 16, 1986

[30] Foreign Application Priority Data

Dec. 16, 1985 [FR] France ................................ 85 18600

[51] Int. Cl.[4] .............................................. A61F 2/22
[52] U.S. Cl. ........................................................ 623/3
[58] Field of Search ............................................. 623/3

[56] References Cited

U.S. PATENT DOCUMENTS

| | | | |
|---|---|---|---|
| 4,105,016 | 8/1978 | Donovan, Jr. ................ | 128/1 D |
| 4,167,046 | 9/1979 | Portner et al. ............... | 3/1.7 |
| 4,195,623 | 4/1980 | Zeff et al. .................... | 128/1 D |
| 4,457,673 | 7/1984 | Conley et al. ................ | 417/412 |
| 4,557,673 | 10/1985 | Chen et al. .................. | 417/412 |
| 4,565,497 | 1/1986 | Miller et al. ................. | 417/63 |
| 4,623,350 | 11/1986 | Lapeyre et al. .............. | 623/3 |
| 4,650,486 | 3/1987 | Chareire ...................... | 623/3 |
| 4,820,300 | 4/1989 | Pierce .......................... | 623/3 |

FOREIGN PATENT DOCUMENTS

| | | |
|---|---|---|
| 0146445 | 6/1985 | European Pat. Off. . |
| 8318368 | 11/1983 | France . |
| 8518425 | 12/1985 | France . |
| 60-18514 | 12/1985 | Japan . |

*Primary Examiner*—Richard J. Apley
*Assistant Examiner*—James Prizant
*Attorney, Agent, or Firm*—Fisher, Christen & Sabol

[57] ABSTRACT

A complete artificial heart is provided including a pericardial pumping module and an extra-pericardial pumping module connected together by a functional connection. In the invention, the mechanism of the extra-pericardial pumping module actuates the pericardial pumping module through gas displacement.

6 Claims, 3 Drawing Sheets

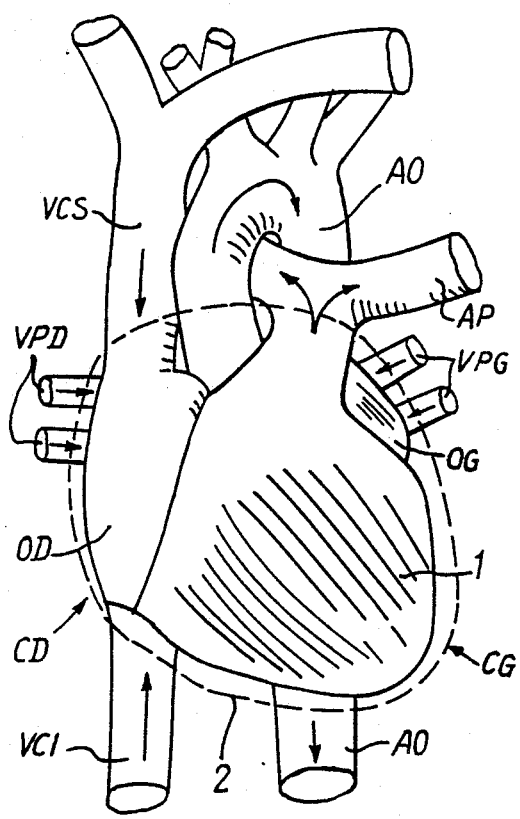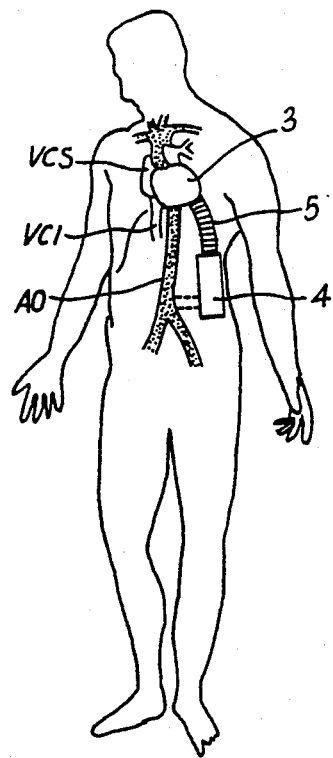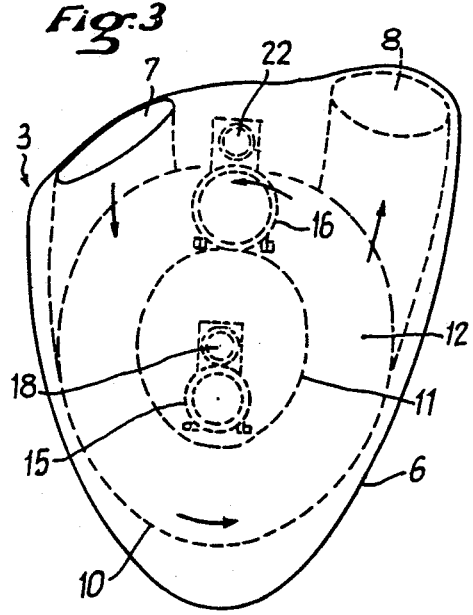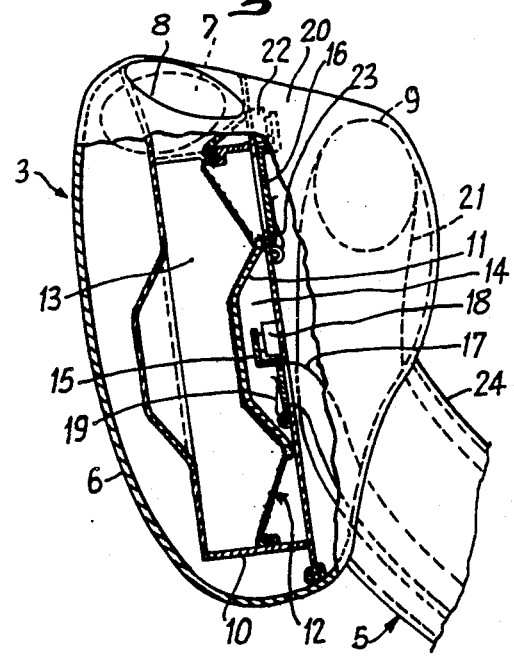

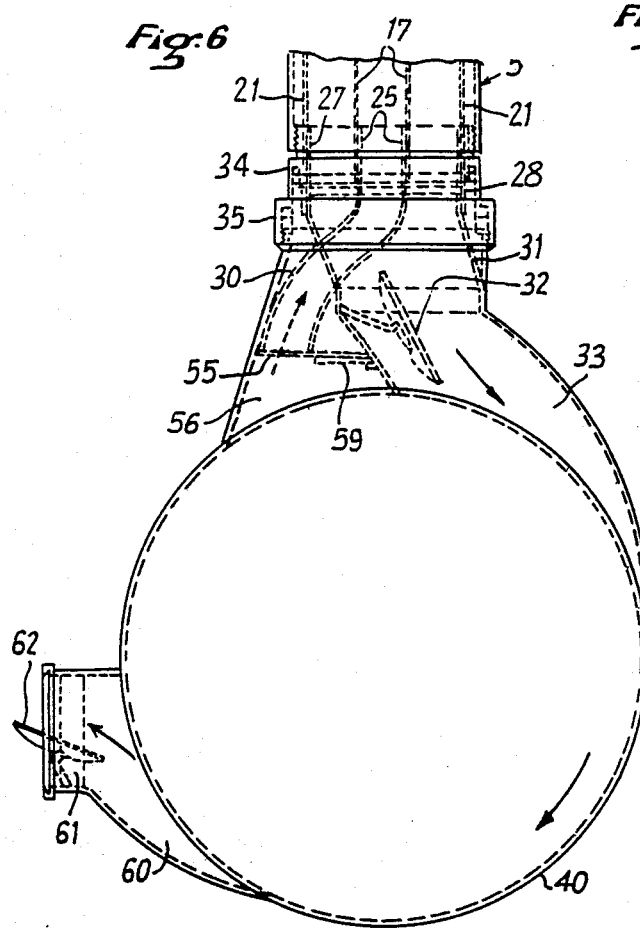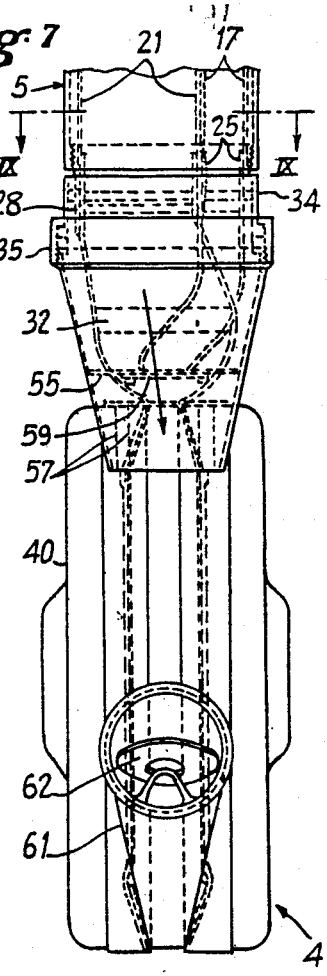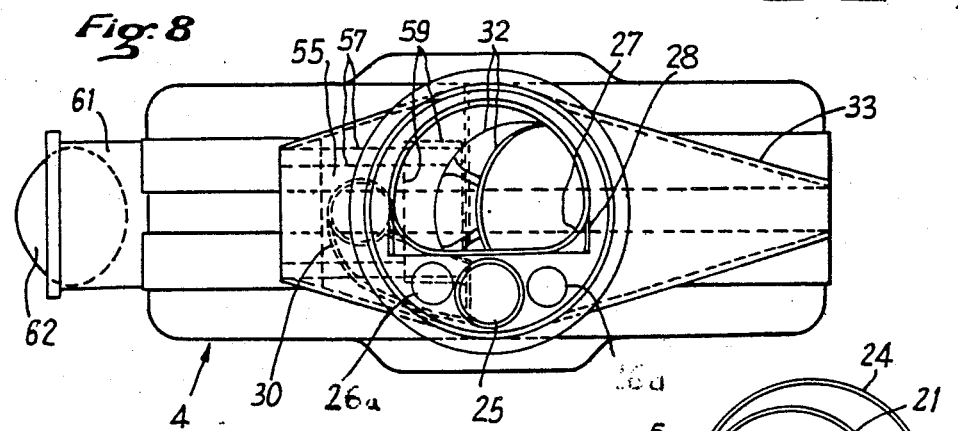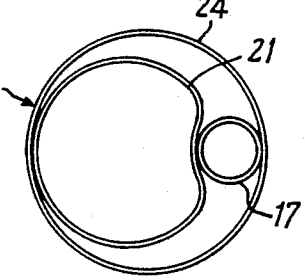

ure, 4,904,255

COMPLETE ARTIFICIAL HEART WITH TWO PUMPING MODULES CONNECTED TOGETHER BY A FUNCTIONAL CONNECTION

BACKGROUND OF THE INVENTION

In the French patent application Nos. 83 18368, filed on the 18 Nov. 1983, (see also U.S. Pat. No. 4,623,350), and No. 85 18425, filed on the 12 Dec. 1985, which corresponds to U.S. Ser. No. 672,376, filed on Nov. 16, 1984, two embodiments have been described of a complete artifical heart including two pumps, representing respectively the right heart and the left heart, this artificial heart being remarkable in that, on the one hand, it comprises the indissociable functional unit formed;

by a pericardial module intended to be housed in the cavity of the natural heart to be replaced and enclosed in a sealed envelope having at least three connection orifices for connection respectively to the right auricle, the pulmonary artery and the left auricle, said orifices for connection to the right auricle and the pulmonary artery being provided with valves serving respectively as inlet port and outlet port to a first pump housed in said pericardial module for providing the function of the right heart of the natural heart to be replaced;

by an extra-pericardial module intended to be housed in a physiological neutral space of the receiving patient and providing the function of the left heart of the natural heart to be replaced, this extra-pericardial module having a sealed envelope in which is enclosed a second pump having an inlet port and an outlet port, each provided with a valve;

by a functional connection between said pericardial and extra-pericardial modules including at least:

a first duct passing through the envelope of said pericardial module and connecting the orifice thereof corresponding to the left auricle and the inlet port of said second pump incorporated in said extra-pericardial module;

a second duct providing gas communication between the sides of said first and second pumps opposed to the blood passing therethrough.

In the first embodiment, the sealed envelope of the pericardial module has a fourth orifice for connection to the aorta and said functional connection includes a third duct passing through the envelope of said pericardial module and connecting said fourth orifice thereof corresponding to the aorta with the outlet port of said second pump incorporated in said extra-pericardial module.

On the other hand, in the second embodiment, the outlet port of said second pump incorporated in said extra-pericardial module is connected directly to the abdominal part of the aorta, so that the fourth orifice of the pericardial module can be omitted as well as said third functional connection duct.

In these two embodiments, each of said pericardial and extra-pericardial pumping modules are advantageously provided in the form of a membrane and pusher plate pump.

SUMMARY OF THE INVENTION

The object of the present invention is to provide a particularly advantageous embodiment of such a complete artificial heart.

To this end, in accordance with the invention, the complete artifical heart having two pumps, representative respectively of the right heart and the left heart and including the indissociable functional unit formed:

by a pericardial module, intended to be housed in the cavity of the natural heart to be replaced and enclosed in a sealed envelope having at least three orifices for connection respectively to the right auricle, to the pulmonary artery and to the left auricle, said orifices for connection to the right auricle and to the pulmonary artery being provided with valves serving respectively as inlet port and outlet port of a first membrane type pump housed in said envelope for providing the function of the right heart of the natural heart to be replaced;

by an extra-pericardial module intended to be housed in a physiologically neutral space of the receiving patient and to provide the function of the left heart of the natural heart to be replaced, this extra-pericardial module including a second pump of the membrane and pusher plate type provided with an actuation system and enclosed in a sealed case, provided with an inlet orifice and an outlet orifice, each equipped with a valve;

by a functional connection between said modules having at least:

a tube passing through said envelope of the pericardial module and connecting the orifice thereof corresponding to the left auricle with the inlet port of the second pump incorporated in said extra-pericardial module;

gas communication means between the sides of said first and second pumps opposed to the blood passing therethrough;

is remarkable in that said communication means include:

a first duct for bringing to said first pump the gas displaced by the second pump so that said displaced gas actuates said first pump in the blood expulsion direction; and a second duct for bringing the gas from the first pump to said second pump.

Thus, the pericardial module comprises no electro-mechanical actuation system but is actuated by the pump of the extra-pericardial module. This is particularly advantageous since the extra-pericardial module may be housed in a physiological space readily accessible by a simple surgical operation and may therefore be easily changed should the actuating system of the pumps fail. On the other hand, since access to the pericardial module is delicate because of the rib cage, it is advantageous that it comprises no mechanical element liable to wear or failure.

In a way already described in the above recalled patent applications, it is advantageous for said functional connection to connect the lower part of the envelope of the pericardial module to the upper part of the extra-pericardial module.

Advantageously, said second duct of the connection between the pericardial and extra-pericardial modules is flexible in the longitudinal direction, but rigid radially and it encloses said first duct, as well as the blood connection tube or tubes between the two modules.

Thus, said second duct serves as mechanical protection for the liquid and gas connection tubes or ducts between said modules. This is particularly advantageous because the tubes connecting the left auricle with the inlet port of the pump of the extra-pericardial module must be very flexible, therefore very thin, and be subject to no provoked pressure drop. This tube, associated with the inner space of said second duct, serves then as complementary left auricle. It will be noted that, because of said second duct, said connection between the modules serves as compliance chamber for the whole of the artificial heart.

Through this second duct may be passed an electric cable connecting said pericardial and extra-pericardial modules together. Thus, the control of the valves of said pericardial module may pass through said extra-pericardial module and said electric cable contained in the connection.

In an advantageous embodiment, said first pump is of the membrane and pusher plate type, and on the side opposite the blood flow of the right heart, these latter define with a case a sealed chamber to which said first and second ducts are connected by means of electro-controlled valves.

The first duct is sealingly secured to said case, whereas said second duct opens into a cavity of the envelope of the pericardial module in connection with said chamber through one of said valves.

Thus, the blood connection tube or tubes between the peri-cardial and extra-pericardial modules may pass through said cavity.

Preferably, said second pump associated with the extra-pericardial module includes, in its case, on the one hand a sealed enclosure in communication with said inlet port and said outlet port of said second pump and defined at least partially by two facing flexible membranes and, on the other hand, two pusher plates facing each other disposed on each side of said sealed enclosure in contact with a membrane and driven with reciprocal movement from and towards each other, under the action of mechanisms arranged respectively on the side of the corresponding pusher plate opposite said sealed enclosure.

In this case, said first and second ducts of the communication means are in communication with said internal parts of said envelope external to said sealed enclosure and containing said actuation mechanisms.

It will thus be noticed that said second pump is formed of two pumping systems acting on the same deformable sealed enclosure, so that, even if one of said systems breaks down, pumping may continue under the action of the other.

Generally, the extra-pericardial module of the artificial heart of the invention may have one or other of the structures described in the French patent application No. 85 18514, filed on the 13 Dec. 1985.

BRIEF DESCRIPTION OF THE DRAWINGS

The Figures of the accompanying drawings show how the invention may be implemented. In these Figures, identical references designate similar elements.

FIG. 1 shows schematically a natural heart connected with its main veins and arteries, in a front view.

FIG. 2 illustrates schematically an artificial heart of the invention in positon in a patient;

FIG. 3 is a schematical front external view of one embodiment of the pericardial module of the invention, for the artificial heart of FIG. 2;

FIG. 4 is a schematical view, in partial section through a plane orthogonal to the plane of FIG. 3, of the pericardial module shown in this last Figure;

FIG. 6 is a side elevational view of the extra-pericardial module of FIG. 5;

FIGS. 7 and 8 are respectively side and top views of the extra-pericardial module of FIG. 5;

FIG. 9 is a section through the line IX—IX of FIG. 7 and

DESCRIPTION OF THE PREFERRED EMBODIMENT

Figure 5:
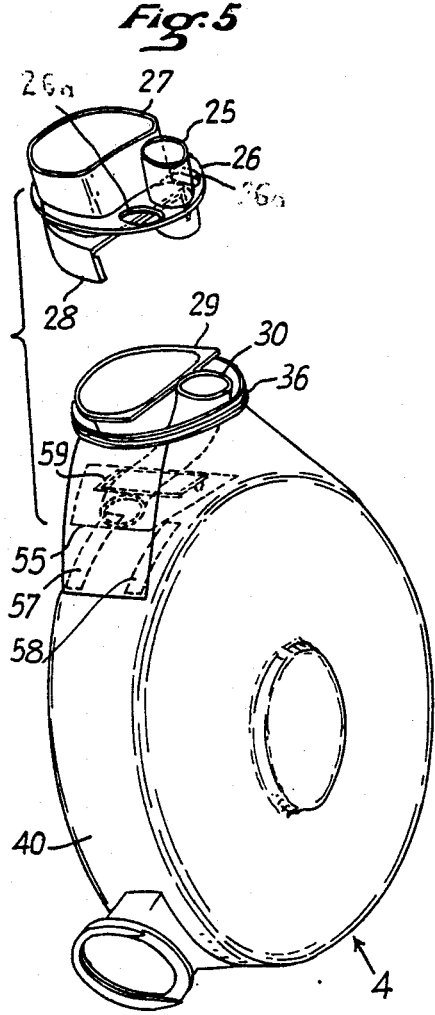
FIG. 5 is an external exploded view in perspective of one embodiment of the extra-pericardial module of the invention, for the artificial heart of FIG. 2.

The embodiment of the artificial heart of the invention shown in FIGS. 2 to 9 and chosen for illustrating the present invention concerns more particularly an embodiment in which the extra-pericardial module is connected directed to the abdominal aorta. However, this arrangement is not obligatory and the present invention applies equally to an artificial heart in which the pericardial module is connected to the thoracic aorta, an additional blood connection being then provided between the pericardial and extra-percardial modules.

As shown schematically in FIG. 1, a natural human heart 1 is housed in the percardial cavity 2 (simply illustrated by a broken line 2) and is actually formed of two separate hearts, but integral with each other, namely the right heart CD including the right auricle OD and the right ventricle and the left heart CG including the left auricle OG and the left ventricle. The auricle OD of the right heart CD receives the venous blood through the upper vena cava VCS and through the lower vena cava VCI, whereas the ventricle of said right heart CD passes the blood thus received through the lungs through the pulmonary artery AP.

Similarly, the auricle OG of the left heart CG receives the blood from the lungs through the left VPG and right VPD pulmonary veins and the ventricle of the left heart CG drives out the blood received through the aorta AO.

The basic idea of the artificial heart with decoupled pumps of the type to which the present invention relates rests on the physiological finding that, although formed of two pumps CD and CG forming a single muscular unit, the heart 1 is in reality formed of two functionally independent assemblies. In fact, from the functional point of view, the right heart CD may be considered as a simple passage heart which pushes a blood column whose flow speed is variable, but never zero, except when the frequencies of beating of heart 1 are very low. When the blood flow of the vascular system increases through an increase in frequency of these heart beats, the participation of the right heart CD in moving the blood through the pulmonary circuit decreases because of the increase in speed and therefore of the kinetic energy of the blood reaching the right heart CD. On the other hand, the left heart CG, through its powerful ventricle, forms the heart properly speaking, that is to say the propulsive pump charged with causing the blood to perfuse in all the organes and tissues of the organism.

As illustrated very schematically in FIG. 2, this complete artificial heart is formed of a functionally indissociable unit including two decoupled pumping modules 3 and 4, but connected together by a tubular functional connection 5.

The pumping module 3, intended to replace the right heart CD of the natural heart 1 is housed in the pericardial cavity 2. It includes a sealed case on which are mounted connections of any known type, for connecting it respectively to the right auricle OD (reservoir of the vena cava VCI and VCS), of the pulmonary artery AP, to the left auricle OG (reservoir of the pulmonary veins VPG and VPD) and, if necessary, to the aorta AO, after cutting them and exeresis of the natural ventricles of the pericardial cavity 2.

The orifices connecting to the right auricle OD and to the pulmonary artery AP are provided with valves serving respectively as inlet port and outlet port of a pump housed in said envelope and intended to provide the function of the right heart of the natural heart to be replaced.

The pumping module 4, intended to play the role of the left heart CG of the natural heart 1, is housed inside the pericardial cavity 2, in a physiologically neutral space, for example the thorax or abdomen. It also has a sealed envelope enclosing a pump with an inlet port and an outlet port, each equipped with a valve.

The functional connection 5, which may pass through the diaphram of the patient receiving the artificial heart without any problem, includes:

a duct providing the connection between the orifice of the pericardial module 3 corresponding to the left auricle OG and the inlet port of the pump incorporated in the extra-pericardial module 4;

if required, when the outlet port of the pump of the extra-pericardial module is not connected directly to the abdominal aorta, a duct providing the connection between the orifice of the pericardial module 3 corresponding to the aorta AO and the outlet port of said pump incorporated in said extra-pericardial module 4;

a gas communication between the sides of the pumps of the pericardial module and of the extra-pericardial module opposed to the blood passing therethrough.

In FIG. 2 has been shown schematically with broken lines the fact that the outlet port of the pump of the extra-pericardial module 4 could be connected directly to the abdominal part of the aorta. In this case, the pericardial module 3 comprises no orifice for connection to the aorta.

The pericardial module 3 of the artificial heart is disposed on a part of the human body which is only accessible through a delicate surgical operation; however, the pumping work which it provides is unimportant. On the other hand, the extra-pericardial module 4 of said artificial heart is disposed in a part of the human body readily accessible at the cost of a simple surgical operation; but the pumping work which it provides is considerable.

Furthermore, since the volume in which the extra-pericardial module is located is appreciable, this latter may be constructed without having to take into account space constraints which are too critical. The actuating mechanism of the extra-pericardial module may then be powerful.

Therefore, the basic idea of the invention is to use this power extra-pericardial mechanism for actuating the pericardial pump which thus may comprise only a minimum of elements subject to wear and failure.

The embodiment of the pericardial module 3 shown in FIGS. 3 and 4 includes a sealed envelope 6 having orifices 7, 8 and 9 (shown schematically) for connection respectively to the right auricle, to the pulmonary artery and to the pulmonary vein of the failing heart to be replaced.

Inside the sealed envelope 6 is disposed a sealed case 10 enclosing a rigid central pumping plate 11 applied against at least flexible membrane 12. The inside of the sealed case 10 is divided into two sealed chambers 13 and 14 by the membrane 12. The sealed chamber 13 is connected to the orifices 7 and 8 by valves not shown whereas the sealed chamber 14 is provided with two electrocontrolled valves 15 and 16.

Valve 15 is sealingly connected to a duct 17 forming part of the connection 15 and intended to convey the gas pressurized by the pump of the extra-pericardial module 4, as will be seen hereafter. Valve 15 is controlled by an electromagnet 18 and is subjected to the action of a return spring 19.

Valve 16 causes chamber 14 to communicate with a cavity 20 of envelope 6 through which the artificial pulmonary vein 21 passes connecting the two modules 3 and 4 together. Valve 16 is controlled by an electromagnet 22 which is subjected to the action of a return spring 23.

The cavity 20 of envelope 6 is in gas connection with module 4 (as will be seen hereafter) through a duct 24, rigid radially but flexible under flexion.

Duct 24 serves as external casing for the connection 5 and it encloses duct 17 and the artificial pulmonary vein 21. If the pericardial module 3 were intended to be connected to the aorta, duct 24 would contain in addition an artificial aorta connecting together the two modules 3 and 4.

When the gas displaced by the pump of the extra-pericardial module 4 arrives through duct 17 into the pericardial module 3, it is compressed because valve 15 is closed. When the gas pressure reaches a sufficient value to be able to supply to the blood the desired curve of physiological pressure, valve 15 opens for the power supplying the electromagnet 18 is cut off. The gas penetrates into the chamber 14 and acts on the rigid pusher plate 11 connected to the flexible membrane 12.

When the volume of blood expelled by the pericardial pump 10, 11 is sufficient, valve 16 opens, for the power supply to the electromagnet 22 is cut and its return spring 23 does not oppose the return of gas to the module 4. During this time, the return spring 19 closes the valve 15 again and the power supplying the electro magnet 18 is reestablished.

This gas return takes place through the part of duct 24 not occupied by ducts 17 and 21, which allows permanent contacting with the atmospheric pressure through the venus pressure which reigns in the flexible and extensible tube 21.

The construction of the pericardial module 3 raises no particular problem.

Envelope 6 may be made from an injected polycarbonate or from a biocompatible metal alloy, electrodeposited for example. Case 10 may be formed by the stamping and welding or by any other method. The inside of this case must be hemocompatible. It may then be coated with carbon deposited by the known method of physical vapor phase deposition or from polyurethane deposited by dipping (for example). The rigid pusher plate 11 may be made from metal or from different plastic materials, for it is always coated with a hemocompatible membrane.

The valves are for example made from metal (titanium, stainless steel, etc. . .). For example, tube 21 is made from polyurethane and tube 17 from elastomer. Tube 24 may be made from a synthetic material reinforced with a steel wire helix.

It can be seen in FIGS. 3 and 4 that the blood flow is never interrupted in module 3 because of the position of the membrane. Thus, as can be seen in FIG. 3, there will always be a blood vortex in the same direction (shown by the arrows). This arrangement allows a good hydraulic efficiency to be obtained and the tendencies to thrombosis to be efficiently combatted.

Furthermore, the membrane may be provided with leak detectors. Should a leak be detected, the alarm is given and, in the case of detection of a serious leak, module 3 is put completely out of service while keeping valves 15 and 16 permanently closed. The blood can then not invade the zone of the motors of the extra-pericardial module 4. The patient will survive this extreme failure, for the return venus pressure is sufficient to provide passage through the right ventricle and the lungs until the surgical operation can be performed.

In FIGS. 5 to 10, one embodiment of the extra-pericardial module 4 has been shown able to cooperate with the above described pericardial module 3. This module 4 includes an envelope 40 inside which is enclosed a pump shown solely in FIG. 10 and which is connected to module 3 by the connection 5.

The flexible duct 17 for the compressed gas is connected to a metal end piece 25. This end piece 25 is welded to a metal plate 26 having another end piece 17 to which is connected the tube 21.

This whole assembly 25, 26 and 27 is welded to a connecting piece 28 which is applied, in the final assembly position, with its inner face against a plate 29. In this position, tube 25 coincides with a rigid tube 30 whose upper end is in the same plane as the surface of plate 29. Tube 30, plate 29 and rigid pipe 31 which extends tube 27 are welded together and are connected by rigid connections to a valve 32 and to a volute 33 for introducing blood into the extra-pericardial module 4.

The piece 34 for fixing tube 24 bears on the seal which exerts an axial force on piece 26 for sealing between tubes 25 and 30 and between pieces 28 and 29. The surface of piece 29 is covered with a very fine soft organic layer so as to promote sliding and sealing during assembly. A clamping nut 35 is screwed onto a screw threaded neck 36 integral with envelope 40.

Figure 10:
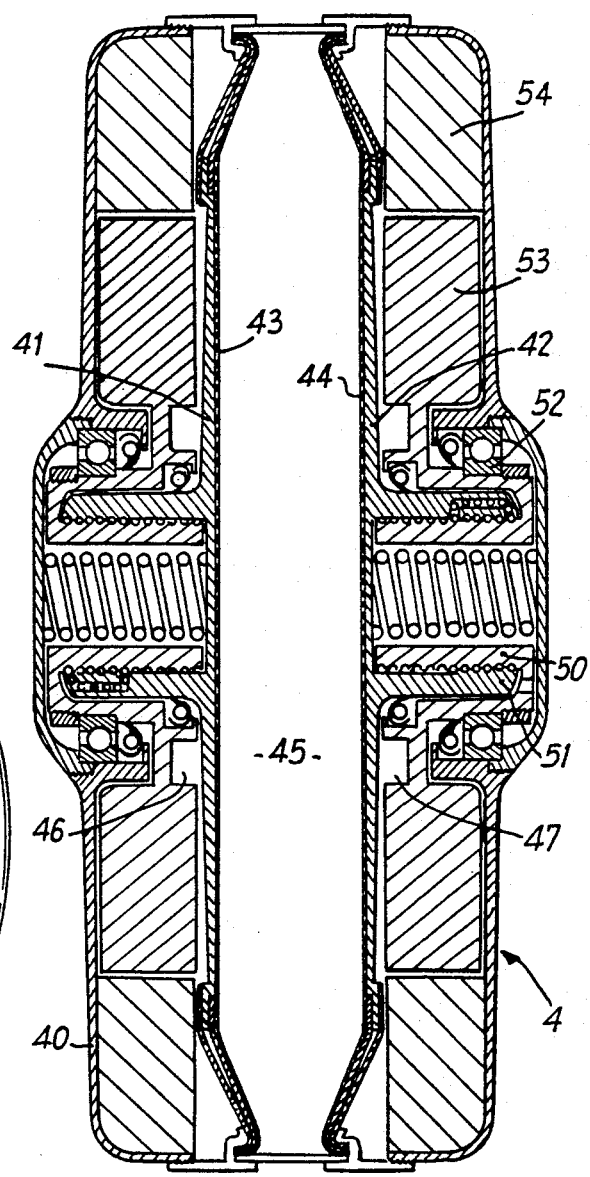
FIG. 10 shows schematically in section one embodiment of the actuation mechanism of the extra-pericardial module of FIGS. 5 to 9.

As shown in FIG. 10, which gives one embodiment of the pumping mechanism of module 4, this mechanism comprises two pusher plates 41 and 42 facing each other which may draw together and away from each other and which bear on flexible membranes 43 and 44 respectively.

With each of the pusher plates 41 and 42 is associated a screw 50 and a ball circulation nut 51 integral with the corresponding pusher plate.

Screw 50 rotates about its axis through a deep groove ball bearing 52 which provides sufficient geometric indexing. Screw 50 is connected to the rotor 53 of a flat electric motor whose annular stator bears the reference 54.

The axial movement of a plate 41, 42 is obtained by rotation of rotor 53 which causes screw 50 to rotate, the plate being secured against rotation by membranes 43 and 44.

Inside envelope 40, the two flexible membranes 43 and 44 define therebetween a single enclosure 45 in connection with the duct (artificial pulmonary vein) 21, in the way described above. In addition, with the envelope 40, the two flexible membranes 43 and 44 define two spaces 46 and 47 external to the sealed enclosure 43. The spaces 46 and 47 are in connection with ducts 17 and 24 in the way which will be described hereafter.

The gas flowing from the extra-pericardial module to the pericardial module passes through the rigid pipe 30 which is sealingly welded to a plate 55 defining an inner volume 56 which communicates with the gas spaces 46 and 47 situated in the extra-pericardial module 4 on the side of the plates 41 and 42 opposite the blood and consequently including the electric motors. Communication with each of the two volumes concerned is provided through orifices 57 and 58 respectively.

As can be seen in FIG. 9, the very flexible and extendable pipe 21 extends freely between the flexible but more rigid forms of ducts 24 and 17. The residual internal volume between ducts 21, 24 and 17 serves for the air return. It depends on the one hand on the blood pressure in the pulmonary vein 21 very much influenced by the atmospheric pressure following passage of the blood into the lungs and, on the other hand, on the opening or closure of valve 32 since the extensibility of pipe 21 allows it to play the role of complementary artificial auricle (which regularizes the pulmonary flow and promotes filling of the left ventricle).

The output of blood towards the aorta takes place through a volute 60 (in connection with cavity 45) and a connection orifice 61 provided with a valve 62.

Thus, it can be seen that in accordance with the invention, the pump of the pericardial module may be actuated by the gas displaced by the extra-pericardial pump.

The following advantages result therefrom:

suppression of the motor activating the pericardial module and so a gain in weight volume for this module;

increasing reliability, for the probability of failures for the assembly of the two modules is scarcely greater than that of the extra-pericardial module alone (and the whole of the breakdowns is generally without serious consequences because of the mechanical redundancy);

possibility of progressively increasing the flow of the pericardial module after the operation, since the exhaust valve 16 may be opened before the complete stroke of the membranes of the extra-pericardial pump has been effected;

reduction of noise and vibrations in the pericard;

good resistance of the inside of the pericardial module to thrombosis because of the possibility of a permanent blood vortex;

good hydraulic efficiency of the pericardial module;

low fatigue of the membranes of the pericardial module and security in the case of damage thereto;

economy in the cost price of the pericardial module;

the fact of actuating the pericardial module by a gas only very slightly penalises the overall efficiency for the power required for actuating this module is very much less than that required by the extra-pericardial module.

What is claimed is:

1. In a complete artificial heart including two pumps, representative respectively of the right heart and of the left heart formed:

by a pericardial module intended to be housed in the cavity of the natural heart to be replaced and enclosed in a sealed envelope having at least three orifices for connection respectively to the right auricle, to the pulmonary artery and to the left auricle, said orifices for connection to the right auricle and to the pulmonary artery being provided with valves for serving respectively as inlet port and outlet port to a first pump of the membrane type housed in said envelope and intend to provide the function of the right heart of the natural heart to be replaced;

by an extra-pericardial module intended to be housed in a physiologically neutral space of the receiving patient and to provide the function of the left heart of the natural heart to be replaced, this extra-pericardial module including a second pump of the membrane and pusher plate type having an actuation system, and being enclosed in a sealed envelope provided with an inlet orifice and an outlet orifice each equipped with a valve;

a functional connection between said modules including at least:

a tube passing through said envelope of said pericardial module and connecting the orifice thereof corresponding to the left auricle with the inlet port of the second pump incorporated in said extra-pericardial module;

gas communication means between the sides of said first and second pumps opposed to the blood passing therethrough;

said communication means including:

a first duct for bringing to said first pump the gas displaced by the second pump, so that said displaced gas actuates said first pump in the blood expulsion direction; and a second duct for bringing the gas from the first pump to said second pump.

2. The artificial heart as claimed in claim 1, wherein said second duct of said connection between the pericardial and extra-pericardial modules is flexible in the longitudinal direction but rigid radially and it encloses said first duct as well as the blood connection tube or tubes between the two modules.

3. The artificial heart as claimed in one of claims 1 or 2, wherein the first pump is of the membrane and pusher plate type and, on the side opposed to the blood flow of the right heart, they define with a case a sealed chamber to which said first and second ducts are connected through electrocontrolled valves.

4. The artificial heart as claimed in claim 3, wherein said first duct is sealingly secured to said case, whereas said second duct opens into a cavity of the envelope of the pericardial module in connection with said chamber through one of said valves.

5. The artificial heart as claimed in claim 1 wherein said second pump associated with the extra-pericardial module includes, in its envelope, on the one hand a sealed enclosure in communication with said inlet port and said outlet port of said second pump and defined at least partially by two flexible facing membranes and, on the other hand, two pusher plates facing each other, disposed on each side of said sealed enclosure in contact with a membrane and driven with a reciprocal movement moving them together and away from each other under the action of mechanisms arranged respectively on the side of the corresponding pusher plate opposite said sealed enclosure.

6. The artificial heart as claimed in claim 5, wherein said first and second ducts of said communication means are in communication with the internal parts of said envelope external to said sealed enclosure and containing said actuation mechanisms.

* * * * *